United States Patent [19]
Hutchinson et al.

[11] Patent Number: 5,377,525
[45] Date of Patent: Jan. 3, 1995

[54] FRICTION TESTING APPARATUS FOR OSCILLATING AT LEAST ONE SPECIMEN IN CONTACT WITH ANOTHER

[76] Inventors: John M. Hutchinson, 82 Meadvale Road, Ealing, London W5 1NR, Great Britain; John C. Hamer, 17 Clive House, Union Grove, London, Great Britain

[21] Appl. No.: 114,427

[22] Filed: Aug. 30, 1993

[30] Foreign Application Priority Data

Sep. 5, 1992 [GB] United Kingdom ............... 9218827

[51] Int. Cl.$^6$ .................... G01N 3/56; G01N 19/02
[52] U.S. Cl. ............................... 73/9; 73/10; 73/794
[58] Field of Search ..................... 73/794, 9, 10

[56] References Cited

U.S. PATENT DOCUMENTS

| | | | |
|---|---|---|---|
| 1,990,771 | 2/1935 | Boden | 73/9 |
| 3,041,868 | 7/1967 | Schaschl et al. | 73/10 |
| 3,643,490 | 2/1972 | Hertel | 73/9 |
| 4,029,122 | 6/1977 | Jaegtnes | 137/551 |
| 4,637,259 | 1/1987 | Jones | 73/794 |
| 4,749,891 | 6/1988 | Sheng | 310/15 |
| 4,788,466 | 11/1988 | Paul et al. | 310/316 |
| 4,966,032 | 10/1990 | Takeuchi | 73/10 |

FOREIGN PATENT DOCUMENTS

| | | | |
|---|---|---|---|
| 0118442 | 5/1991 | Japan | 73/9 |
| 678456 | 9/1952 | United Kingdom . | |
| 2155560 | 9/1983 | United Kingdom . | |
| 2162953 | 9/1983 | United Kingdom . | |
| 1601560 | 10/1990 | U.S.S.R. | 73/9 |
| 1605176 | 11/1990 | U.S.S.R. | 73/9 |

OTHER PUBLICATIONS

Sakamoto et al, "A Friction Apparatus for Measuring the Normal Displacement of a Sliding Body", J. Phys. E: Sci. Instruments, vol. 13, 1980, pp. 1017–1020.

Primary Examiner—Hezron E. Williams
Assistant Examiner—James M. Olsen
Attorney, Agent, or Firm—Herbert Dubno

[57] ABSTRACT

The invention relates to a test apparatus for carrying out analysis on fluids or components comprising two specimens which are movable with respect to each other by means of an oscillating driving means. Means are provided for applying a measurable load between the two specimens. The oscillating driving means further comprises a stiffness adjusting means in order to control the degree of lateral movement of the oscillating driving means. The test apparatus also comprises a force measuring means which is connected to a support which is relatively much heavier than the oscillating driving means and the specimens in order that accurate results are achieved.

20 Claims, 3 Drawing Sheets

FRICTION TESTING APPARATUS FOR OSCILLATING AT LEAST ONE SPECIMEN IN CONTACT WITH ANOTHER

FIELD OF THE INVENTION

This invention relates to apparatus for testing the lubricating properties of lubricants and/or the frictional and wear properties of materials. The apparatus simulates the conditions of operation of a mechanical device having moving parts and a fluid lubricant, such as for example a fuel pump. Measurements can be made of the condition of the lubricant, the condition of the moving parts and the forces acting on the moving parts during the test. From these measurements it is typically possible to test new materials and lubricants before introduction into new products.

BACKGROUND OF THE INVENTION

Known types of apparatus are found to operate at relatively high loads of typically up to 1400 N. A consequence of these high loads is that the apparatus must be made sufficiently sturdy to carry the loads and drive the specimens against the resulting high frictional forces. This in turn means that the oscillating components of the apparatus must be relatively heavy. Having relatively large masses oscillating at frequencies of more than a few Hertz requires generation of substantial inertial forces which must react against the body of the apparatus. These inertial forces give rise to unwanted vibrations in the body of the apparatus which interfere with the accurate measurement of the frictional forces between the specimens.

A previous disclosure UK patent No 2162953, describes a method of reducing this unwanted vibration in the force measuring system by vibration isolation means. However, since the magnitude of the unwanted vibration depends only on the frequency and displacement amplitude of the oscillating masses and not on the load, when tests are carried out at low loads even very small unwanted vibrations can completely swamp the frictional forces of interest.

Another serious problem with known devices is that they give rise to problems of stroke length consistency under conditions of varying friction coefficient between the test specimens, especially at stroke lengths of less than 0.1 mm. The frictional forces generated in a sliding contact are inherently non-linear with respect to the sliding velocity or displacement. This means that at short stroke lengths there is a tendency for stick-slip behavior to occur, which can be difficult to control. Known apparatus which use mechanical linkages to drive the moving specimen do not suffer from this problem but cumulative tolerance errors in the linkage mean that accurate short stroke lengths are difficult to achieve with good reproducibility.

SUMMARY OF THE INVENTION

An apparatus according to the invention includes two specimens which can be oscillated in sliding contact against each other at frequencies of between 5 and 400 Hz while pressed into contact by an adjustable load. Provision is made to measure the frictional forces generated between the samples. The apparatus enables rapid assessment to be made of the properties of any lubricant between the specimens and of the material properties of the specimens themselves.

According to the present invention there is provided a test apparatus comprising a first specimen holder which is adapted to hold a first specimen such that a surface of the said specimen is in contact with a second specimen, in a second specimen holder, said test apparatus also comprising oscillatory driving means which comprises an oscillating arm which oscillates backwards and forwards in a direction perpendicular to the line of contact between the two specimens and which is connected to said first specimen holder, said second specimen holder being connected to a force measuring means. According to the invention the force measuring means is connected to a support whose mass is at least ten times as great as the combined mass of the oscillating arm and the second specimen holder.

According to the present invention there is provided a test apparatus comprising: a first specimen holder which is adapted to hold a first specimen such that a surface of the said specimen is in contact with a second specimen, in a second specimen holder, means for applying a measurable load between the two specimens, said test apparatus also comprising oscillatory driving means for oscillating at least one of the specimen holders along a direction substantially perpendicular to the line of contact between the specimens, wherein said oscillating driving means comprises an electromagnetic vibrator. The oscillating driving means can further comprise a stiffness adjusting means.

According to a further aspect of the invention one or more flexural members are provided which provide an adjustable spring stiffness to pre-load the oscillatory driving means. According to the invention a test apparatus is provided in which the oscillatory driving means is variable in frequency and amplitude.

Typically the force measuring means will comprise a piezoelectric force transducer connected to the fixed specimen.

According to the invention a test apparatus is provided in which the first and second specimens are electrically insulated from each other when they are not in contact and that the test apparatus further comprises a means of measurement of the electrical resistance between the test specimen and the test surface.

The fixed specimen holder is supported by a flexure which is relatively stiff in all directions except in the direction of relative sliding of the specimens in which direction it is designed to be much less stiff than the force measuring means. This ensures that the frictional force between the samples is almost entirely carried by the force measuring means and not by the fixed specimen holder support. Typically the oscillatory driving means will comprise an electromagnetic vibrator.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
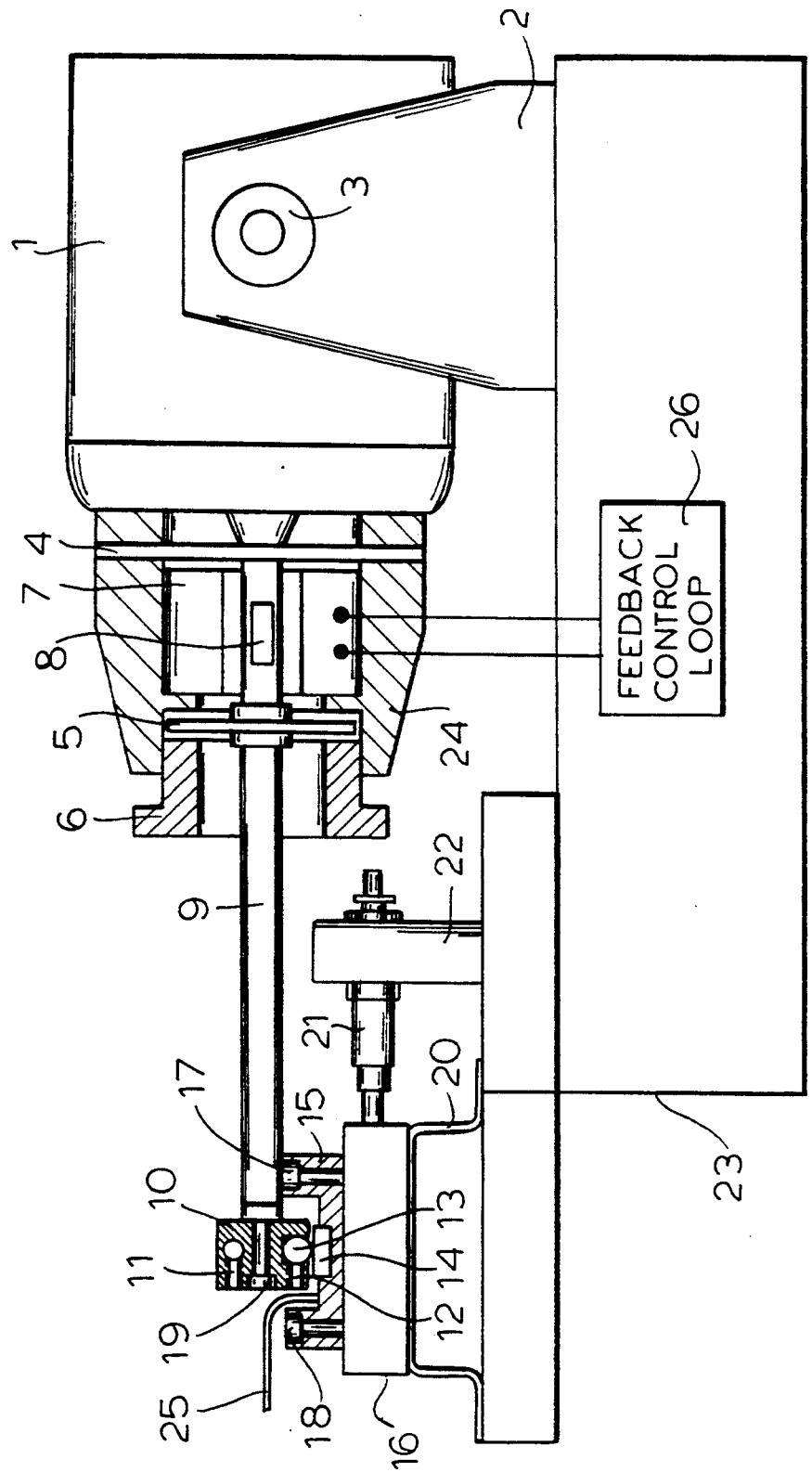
FIG. 1 is a part longitudinal section of an embodiment of the apparatus in accordance with the invention taken along the line I—I in FIG. 2.
Figure 2:
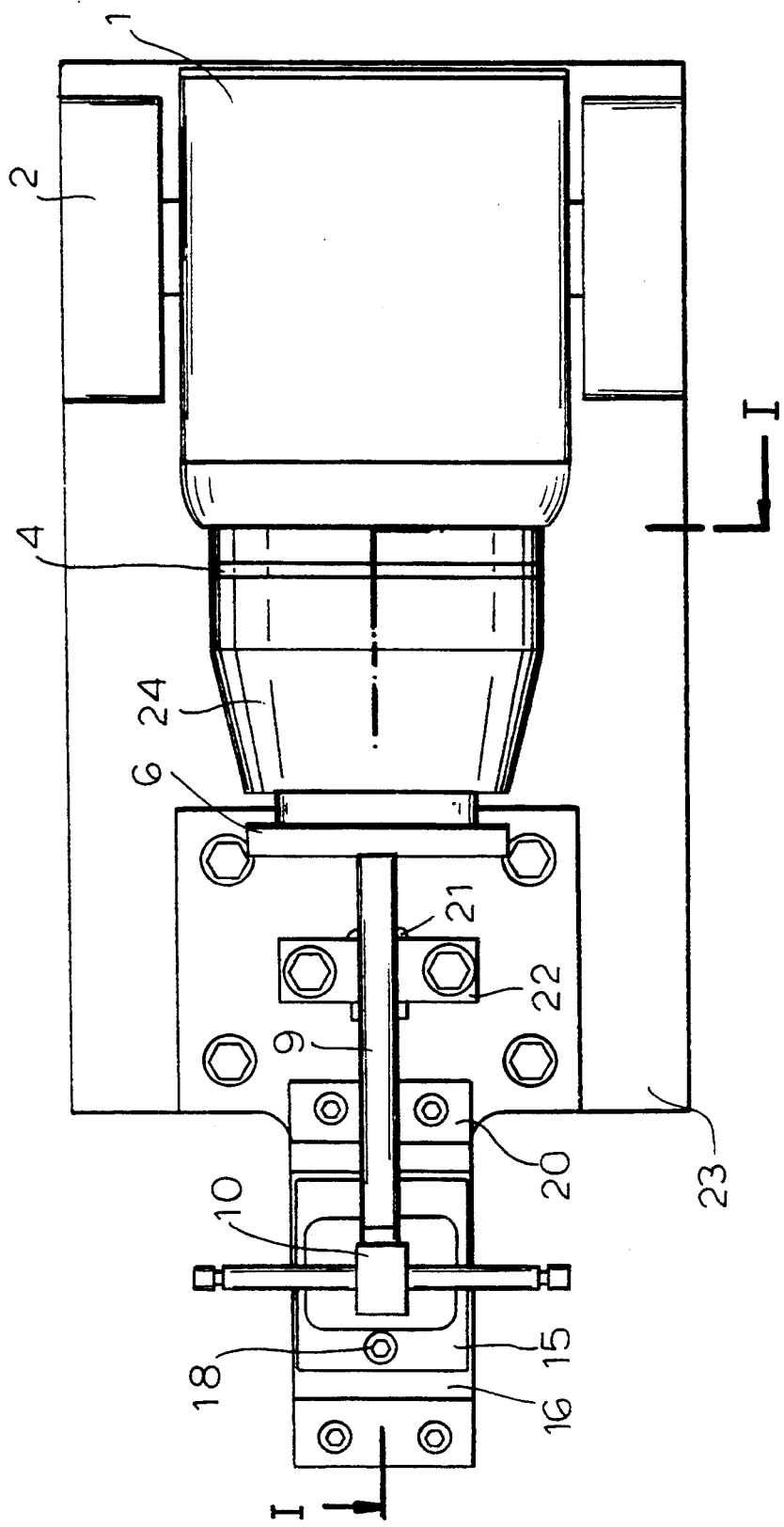
FIG. 2 is a plan view of one embodiment of the apparatus in accordance with the invention.
Figure 3:
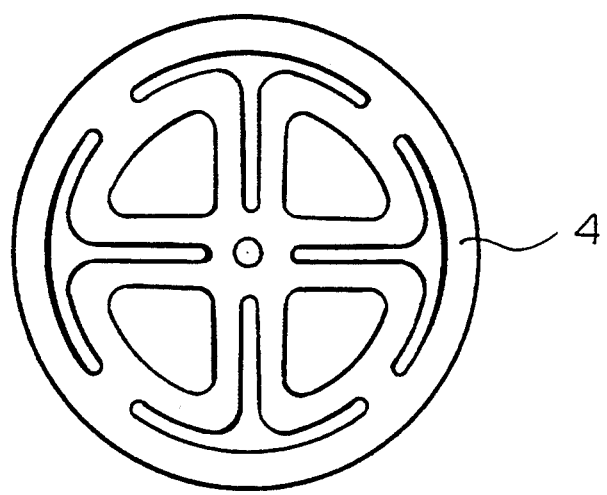
FIG. 3 is a cross section through the flexure of FIG. 1.
Figure 4:
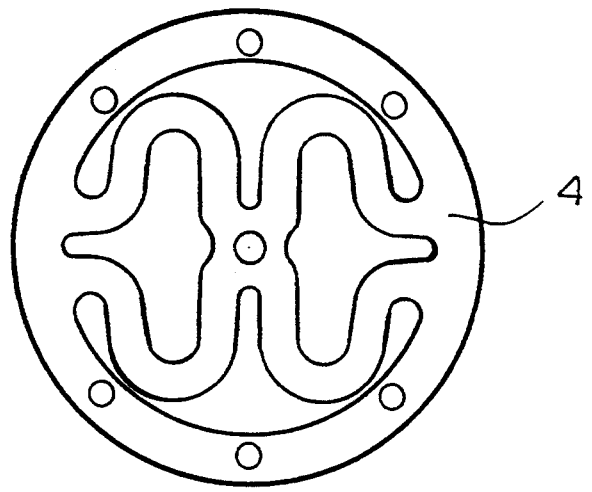
FIG. 4 is a cross section of a further embodiment through the flexure of FIG. 1.

The drawing shows an embodiment of test apparatus according to the present invention having upper and lower specimens 13 and 14 respectively. The upper specimen 13 is releasedly held in the upper specimen holder 10 by a grub screw 12. The upper specimen 13 comprises a sphere of the material under test. The upper specimen holder 10 is releasedly attached by a screw 19 to a push rod 9 connected to the electromagnetic vibrator 1. The push rod 9 is in the form of a hollow tube of for example aluminum or carbon fiber composite, chosen to have low mass and high stiffness.

A rear flexure 4 is attached to the push rod 9 and clamped around its outside edge in housing 24. The rear flexure 4 acts to increase the axial stiffness of the vibrator 1. A forward flexure 5 is designed to be about 10 times stiffer in the axial direction than the rear flexure 4 and is attached to the push rod 9 but free at its outside edge when operating at stroke lengths of more than 0.2 mm.

The displacement measuring means will typically be a Linear Variable Differential Transformer (LVDT) which will be incorporated into an electrical feedback circuit to control the amplitude of oscillation of the vibrator. Conveniently one or more flexures may be incorporated along the axis of oscillation of the vibrator and specimen holder such that the flexures resist the oscillation of the specimen holder. These flexures may comprise a spring stiffness only, or a spring and damper in parallel, or a damper only. The flexures apply a resistance to the motion of the movable specimen holder which is linear with respect to displacement and/or velocity and thus reduce the proportion of the total load on the vibrator which is contributed by the non-linear frictional force between the specimens. Thus a change of, for example 50% in the frictional force between the specimens will only result in a change of approximately 5% in the total load experienced by the vibrator. The effect is thus to reduce the sensitivity of the stroke length to changes in the non-linear frictional load and allow reliable operation at very short stroke lengths.

In any case the oscillatory driving means will suitably be variable in frequency and amplitude to known values.

When it is desired to operate the vibrator 1 at stroke lengths of less than 0.2 mm, for example when carrying out fretting tests, the threaded collar 6 is screwed into housing 24, clamping the outside edge of forward flexure 5 against the housing 24 and thus increasing the axial stiffness of the vibrator 1 by about 10 times. This permits reliable operation at stroke lengths of 10 microns or less.

Appropriate adjustments can be made to the flexures to adjust the axial stiffness, in ways which will be apparent to those skilled in the art to achieve reliable operation at stroke lengths between 10 microns and 0.2 mm.

In order to measure and control the stroke length of the vibrator 1 a linear variable differential transformer (LVDT) 7 is held in housing 24 with the push rod 9 running through its center. The LVDT core 8 is held rigidly inside the push rod 9 so that it is axially and longitudinally central inside the LVDT 7 when the push rod 9 is at rest. The push rod 9 is preferably made of non-magnetic material to allow the LVDT 7 to operate correctly. In use the LVDT 7 detects the motion of the core 8 and hence the push rod 9 and upper specimen holder 10 and a feedback control circuit 26 is used to regulate the power to the vibrator to maintain the stroke length at any desired value, irrespective of changes in the friction coefficient between the specimens.

The vibrator 1 is pivoted on two bearings 3 held in supports 2. The base block 23 is designed to be approximately 500 times more massive than the total mass of all the oscillating components of the apparatus. This is easy to achieve while keeping the total mass of the apparatus low enough to be hand portable because the total oscillating mass is only about 40 grams. This ensures that the inertial forces reacted against the vibrator 1 by the oscillating masses will only give rise to tiny accelerations in the body of the apparatus and do not disturb the measurements of friction force.

Load is applied to the specimens by means of dead weights suspended from load pin 11. Alternatively an adjustable spring balance system could be used. The lower specimen 14 is releasedly clamped into the lower specimen holder 15. This specimen holder is in the form of a small stainless steel bath which can contain a small volume of test lubricant. The specimen holder is releasedly clamped onto the heater block 16 by screws 17 and 18.

The temperature regulating block 16 contains electric heaters or cooling elements which together with thermocouple 25 and a suitable controller allow tests to be carried out at elevated temperatures or reduced temperatures. The temperature regulating block 16 is attached to a flexural support 20 which is designed to be stiff in all directions except the direction of oscillation of the upper sample 13, in which direction it is allowed to deflect. The motion of the temperature regulating block 16 and lower sample holder 15 in this direction is restrained by the force transducer 21 attached to a rigid block 22.

Suitably the lower, fixed specimen holder may be in the form of a stainless steel bath to contain the test lubricant. The specimen holder may be attached to a block containing electrical heaters and/or galleries for cooling fluids which together with suitable control means will allow tests to be carried out at temperatures other than room temperature. The specimen holder may also be enclosed in a chamber to allow tests to be carried out in specific gas atmospheres. Suitably the apparatus further comprises means for applying a variable known load to press the specimens into contact.

Since the force transducer 21, for example a piezo electric force transducer, is many orders of magnitude stiffer than the flexural support 20 in the direction of oscillation of the upper sample 13 the frictional forces between the specimens will be reacted almost entirely against the force transducer 21. The force transducer 21 is connected to an electronic circuit which provides instantaneous and time averaged friction force outputs. By means of this apparatus it is also possible to measure the electrical resistance of the contact between the two specimens. This resistance is determined by the degree of asperity to asperity contact between the specimens and is a qualitative measure of the effectiveness of the lubricant at separating the specimens.

During these measurements it is possible to vary the parameters of load and specimen temperature by the methods described above.

We claim:

1. A test apparatus comprising:
    a first specimen holder which is adapted to hold a first specimen such that a surface of the said specimen is in contact with a second specimen, in a second specimen holder;

means for applying a measurable load between the specimens;

oscillatory driving means for oscillating at least one of the specimen holders along a direction substantially perpendicular to a line of contact between the specimens, said oscillating driving means comprising an electromagnetic vibrator and a stiffness adjusting means, the first and second specimen being electrically insulated from each other when they are not in contact; and means for measurement of electrical resistance between the test specimens.

2. A test apparatus according to claim 1 wherein the test apparatus comprises displacement measuring means to determine an amplitude of oscillation of the specimen.

3. A test apparatus according to claim 2 wherein said displacement measuring means is a linear variable differential transformer.

4. A test apparatus according to claim 2 wherein said displacement measuring means is connected to a feedback circuit to control the amplitude of vibration of the oscillatory driving means.

5. A test apparatus according to claim 1, further comprising means for controlling the amplitude of oscillation of said at least one specimen.

6. A test apparatus according to claim 1, further comprising force measuring means to measure the frictional force between the specimens.

7. A test apparatus according to claim 1 wherein the stiffness adjusting means comprises at least one flexural member.

8. A test apparatus according to claim 7 wherein said at lest one flexural member can be engaged and disengaged.

9. A test apparatus according to claim 7 wherein a spring stiffness of the said at lest one flexural member is adjustable.

10. A test apparatus according to claim 1 wherein said oscillatory driving means is variable in frequency and amplitude.

11. A test apparatus according to claim 1 wherein at least one of the test specimens is provided in a tank for containing a test lubricant.

12. A test apparatus according to claim 1 further comprising a temperature regulating means in order to carry out tests at various temperatures.

13. A test apparatus designed to stimulate the conditions of operation of a mechanical device having moving parts, such as for example a pump, for the purposes of determining the extent of wear on the moving parts comprising:

a first specimen holder which is adapted to hold a first specimen such that a surface of the said specimen is in contact with a second specimen, in a second specimen holder, means for applying a measurable load between the two specimens, said test apparatus also comprising oscillatory driving means for oscillating and connected to at least one of the specimen holders along a direction substantially perpendicular to the line of contact between the specimens, wherein said oscillating driving means comprises an electromagnetic vibrator and wherein the oscillating driving means further comprises a stiffness adjusting means.

14. A test apparatus according to claim 13 wherein the test apparatus comprises displacement measuring means to determine an amplitude of oscillation of the specimen.

15. A test apparatus according to claim 14 wherein said displacement measuring means is a linear variable differential transformer.

16. A test apparatus according to claim 13, further comprising means for controlling the amplitude of oscillation of said at least one specimen.

17. A test apparatus according to claim 13, further comprising force measuring means to measure the frictional force between the specimens.

18. A test apparatus according to claim 13 wherein the stiffness adjusting means comprises at least one flexural member.

19. A test apparatus according to claim 18 wherein said at lest one flexural member can be engaged and disengaged.

20. A test apparatus according to claim 18 wherein a spring stiffness of the said at lest one flexural member is adjustable.

* * * * *